United States Patent [19]

Berger et al.

[11] 4,328,376

[45] May 4, 1982

[54] METHOD OF REMOVING FLUORINATED OLEFIN BYPRODUCT FORMED DURING THE SYNTHESIS OF A FLUORINATED ETHER

[75] Inventors: Arthur Berger, Skokie, Ill.; Robert L. Simon, San Carlos, Calif.

[73] Assignee: Baxter Travenol Laboratories, Inc., Deerfield, Ill.

[21] Appl. No.: 135,428

[22] Filed: Mar. 31, 1980

[51] Int. Cl.$^3$ .............................................. C07C 41/34
[52] U.S. Cl. .................................. 568/682; 570/238; 570/262
[58] Field of Search ......................... 568/682, 683, 686

[56] References Cited

U.S. PATENT DOCUMENTS 2,691,052 10/1954 Cines .................................... 268/682
3,683,092 8/1972 Regan et al. ......................... 568/683
3,689,571 9/1972 Regan et al. ......................... 568/683

OTHER PUBLICATIONS

Lovelace et al., Aliphatic Fluorine Compounds, Reinhold Publishing Corporation, New York, 1958, pp. 265, 262.
Coffman et al., J. Org. Chem., 14, 1949, pp. 747–749.

*Primary Examiner*—Howard T. Mars
*Attorney, Agent, or Firm*—Max D. Hensley; Paul C. Flattery; John P. Kirby, Jr.

[57] ABSTRACT

The method of removing fluorinated olefin byproduct formed during the synthesis of a fluoromethylhexafluoroisopropyl ether product or the like comprises: adding ammonia or an amine to the mixture to react with the fluorinated olefin byproduct, and thereafter distilling the fluoromethylhexafluoroisopropyl ether product to remove it from the byproduct.

11 Claims, No Drawings

METHOD OF REMOVING FLUORINATED OLEFIN BYPRODUCT FORMED DURING THE SYNTHESIS OF A FLUORINATED ETHER

BACKGROUND OF THE INVENTION

Fluoromethyl-1,1,1,3,3,3-hexafluoroisopropyl ether, as described in U.S. Pat. Nos. 3,689,571 and 3,683,092, is an anesthetic which is showing very promising results in clinical trial, being non-inflammable under conditions of use, and having advantages that appear to greatly outweigh any minor disadvantage.

For clinical use, it is necessary of course to produce the above ether material in large quantities, for example, by a synthesis technique as described in the above patents, and the abandoned original application, Ser. No. 771,365 filed Oct. 28, 1978, from which the above-cited U.S. patents claim priority.

On scaled-up synthesis runs for the production of larger quantities of fluoromethyl-1,1,1,3,3,3-hexafluoroisopropyl ether, an undesirable fluorinated olefin byproduct has been detected in small quantities, for example, about 0.4 percent by weight. Since the ether material is intended for use as a clinical anesthetic, it is necessary to completely remove the olefin byproduct prior to administration to a patient.

The prime olefin byproduct produced with the ether material has a molecular weight of 314 by mass spectrometry, and has been tentatively identified as having a structure as follows (although the specific structure of the olefin impurity is not intended to limit the scope of this invention): $CF_3C(CF_3)=CH-CH(CF_3)_2$.

The NMR spectrum obtained by us for the byproduct impurity corresponds to that reported by Yu. E. Aronov, et al. for the olefin product identified above (Izvestiya Akademii Nauk, SSSR, Seriga Khimicheskaya, No. 8, pp. 1758–1768 (1967).

The problem of the separation of this byproduct has been that it distills together with the ether, possibly as an azeotrope, which makes it essentially impracticable to separate the two materials by distillation.

In accordance with this invention, an effective technique for the removal of the fluorinated olefin byproduct is provided, as well as effective techniques for removal of the reactants used.

In the preferred instance, the reactant used is a physiological material which is easily removed from the product.

DESCRIPTION OF THE INVENTION

In accordance with this invention, the fluorinated olefin byproduct formed during the synthesis of fluoromethylhexafluoroisopropyl ether products or the like is removed by adding a nucleophilic material selected from, but not limited to, the group consisting of ammonia, primary amines, and secondary amines which combine with the fluorinated olefin byproduct so that a separation from the ether product may be easily made. Thereafter, the fluoromethylhexafluoroisopropyl ether product may be removed from the treated byproduct, for example by distillation.

Preferably, the fluorinated olefins which are most readily removed by the invention of this application are those which contain an olefinic carbon linkage in which one of the participating carbon atoms is bonded to one or more $-CF_3$ or $-CF_2-$ groups, for example, trifluoromethyl.

Specifically, the structure of fluorinated olefins which are most readily removed by the invention of this application may be expressed by:

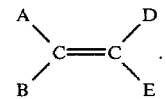

C represents carbon atoms which participate in the olefin linkage, while A and B may comprise di-or trifluorinated carbon atoms bonded to one of the olefin carbon atoms. For example, A and/or B may be trifluoromethyl, difluoromethyl, or 1,1-difluoroethyl, by way of example.

Units D and E may be any of a variety of groups, for example, fluorine, chlorine, hydrogen, methyl, or 1,1,1,3,3,3-hexafluoroisopropyl, by way of example.

Preferably, ammonia is the material used, because of its known physiological characteristics and low toxicity, plus its easy neutralization and/or removal from the system. Ammonia derivatives such as ammonium hydroxide may also be used as equivalent materials, and are intended to be included in this invention.

It may be preferred to add a molar excess of ammonia, preferably at least 1.5 times the molar amount of fluorinated olefin byproduct.

Alternatively, primary and secondary amines may be used. For example, aniline (a primary aromatic amine) or benzylmethylamine (an aromatic secondary amine) may be used. Likewise, aliphatic secondary amines such as diethylamine, piperidine, or aliphatic primary amines such as hexylamine or dodecylamine may also be used.

An acid may be used in dilute water solution for washing residual amounts of amine or ammonia out of the ether product. The acid may be any preferably physiologically compatible one such as dilute hydrochloric acid, acetic acid, citric acid, or the like.

The following examples are offered for illustrative purposes only, and are not intended to limit the scope of this invention, which is as defined in the claims below.

EXAMPLE 1

A portion of fluoromethyl-1,1,1,3,3,3-hexafluoroisopropyl ether, containing a minor amount (about 0.4 percent by weight) of a fluorinated olefin byproduct, was treated with a ten molar excess of piperidine, based on the molar concentration of fluorinated olefin impurity present.

The mixture was stirred for at least 30 minutes, and then distilled at atmospheric pressure. The distillate of the desired ether product was obtained essentially free of olefin impurity.

The unreacted piperidine which was entrained in the distillate was removed by passing the distillate through an acid-washed alumina column or by washing the impure fluorinated ether product with dilute hydrochloric acid or other aqueous physiologically compatible acid before redistillation. The product was of high purity.

EXAMPLE 2

A portion of fluoromethyl-1,1,1,3,3,3-hexafluoroisopropyl ether, containing a minor amount (about 0.4 percent by weight) of a fluorinated olefin byproduct, was synthesized in accordance with known techniques by chlorination of methyl-1,1,1,3,3,3-hexafluoroisopropyl ether, followed by fluorination of the chloromethyl portion of the ether by means of potassium fluoride.

Approximately 170 ml. of the resulting product, containing the olefin byproduct, was placed in a flask, which, in turn, was placed in an ice bath. Then, 21.7 grams of ammonia were bubbled through the material over a period of two hours. At this time gas chromatographic analysis could no longer detect the olefin byproduct, indicating complete reaction of the olefin material with the ammonia.

Nitrogen gas was bubbled through the reaction mixture to remove excess ammonia. Following this, 170 ml. of the ammonia-treated product was poured into a 500 ml. separatory funnel and washed three times with 170 ml. of 1N. sulfuric acid. Following this, the mixture was washed with 170 ml. of dilute sodium bicarbonate solution, followed by three washes each with 170 ml. of water, which provided a wash water which was neutral to pH paper.

The clear, colorless product was then decanted into a 200 ml. Erlenmeyer flask containing anhydrous sodium sulfate to serve as a water absorbing agent. After stirring, the mixture was poured into a 200 ml. round bottom flask. TTitration of a sample of the material at this stage showed it to be free of alkali.

The round bottom flask was connected to distillation apparatus and heated. The receiving flask, a 200 ml. Erlenmeyer flask, was cooled in an ice bath at the receiving end.

The majority of the material was distilled at essentially 57° C., 217.2 grams being collected. The distillate was essentially pure fluoromethyl-1,1,1,3,3,3-hexafluoroisopropyl ether, being free of the olefin byproducts.

A 5.5 gram residue remained behind after the distillation process, which was believed to include the reaction product of the olefin and ammonia.

That which is claimed is:

1. The method of removing fluorinated olefin byproduct formed during the synthesis of fluoromethylhexafluoroisopropyl ether product, which comprises adding a material selected from the group consisting of ammonia and primary and secondary amines to said product, to react with said fluorinated olefin byproduct, and thereafter distilling said fluoromethylhexafluoroisopropyl ether product to separate it from the treated byproduct, and removing any residual traces of said material from the ether product.

2. The method of claim 1 in which said fluoromethylhexafluoroisopropyl ether product is passed after distillation through an acid-washed alumina column.

3. The method of claim 1 in which said fluoromethylhexafluoroisopropyl ether product is washed after reaction and prior to distillation with a dilute physiologically compatible aqueous acid.

4. The method of claim 1 in which a water soluble amine is added.

5. The method of claim 1 in which ammonia is the material added to said product.

6. The method of claim 5 in which the molar amount of ammonia added, compared with the molar amount of fluorinated olefin byproduct present, is at least 150 percent.

7. The method of removing fluorinated olefin byproduct formed during the synthesis of fluoromethyl-1,1,1,3,3,3-hexafluoroisopropyl ether product, which comprises: adding ammonia to said product to react with said fluorinated olefin byproduct, washing said fluoromethylhexafluoroisopropyl ether product with dilute, aqueous physiologically compatible acid, and thereafter distilling said fluoromethyl-1,1,1,3,3,3-hexafluoroisopropyl ether product to separate it from the byproduct.

8. The method of claim 1 in which said fluorinated olefin contains an olefinic carbon linkage in which at least one of the participating carbon atoms is also bonded to at least one other carbon atom which, in turn, is bonded to at least two fluorine atoms.

9. The method of claim 7 in which said fluorinated olefin contains an olefinic carbon linkage in which at least one of the participating carbon atoms is also bonded to at least one other carbon atom, which, in turn, is bonded to at least two fluorine atoms.

10. The method of claim 1 in which said fluorinated olefin byproduct consists essentially of a material of the formula $CF_3C(CF_3)=CH-CH(CF_3)_2$.

11. The method of claim 7 in which said fluorinated olefin byproduct consists essentially of a material of the formula $CF_3C(CF_3)=CH-CH(CF_3)_2$.

* * * * *